US011484869B2

(12) United States Patent
Koseoglu et al.

(10) Patent No.: US 11,484,869 B2
(45) Date of Patent: Nov. 1, 2022

(54) MODIFIED ULTRA-STABLE Y (USY) ZEOLITE CATALYST FOR DEALKYLATION OF AROMATICS

(71) Applicants: Saudi Arabian Oil Company, Dhahran (SA); JGC Catalysts and Chemicals Ltd., Kanagawa (JP); Japan Cooperation Center, Petroleum, Tokyo (JP)

(72) Inventors: Omer Refa Koseoglu, Dhahran (SA); Robert Peter Hodgkins, Dhahran (SA); Mitsunori Watabe, Kawasaki (JP); Koji Uchida, Kawasaki (JP)

(73) Assignees: Saudi Arabian Oil Company, Dhahran (SA); JGC Catalysts and Chemicals Ltd., Kanagawa (JP); Japan Cooperation Center, Petroleum, Tokyo (JP)

( * ) Notice: Subject to any disclaimer, the term of this patent is extended or adjusted under 35 U.S.C. 154(b) by 184 days.

(21) Appl. No.: 17/116,856

(22) Filed: Dec. 9, 2020

(65) Prior Publication Data

US 2022/0176357 A1 Jun. 9, 2022

(51) Int. Cl.
*B01J 29/08* (2006.01)
*B01J 21/04* (2006.01)
*C07C 4/18* (2006.01)

(52) U.S. Cl.
CPC ........... *B01J 29/088* (2013.01); *B01J 21/04* (2013.01); *C07C 4/18* (2013.01); *B01J 2229/26* (2013.01)

(58) Field of Classification Search
CPC ........ B01J 21/04; B01J 21/063; B01J 21/066; B01J 23/883; B01J 29/088; B01J 29/146; B01J 29/166; B01J 2229/16; B01J 2229/26; C07C 4/18; C07C 2529/08; C07C 2529/14; C07C 2529/16; C10G 45/64
See application file for complete search history.

(56) References Cited

U.S. PATENT DOCUMENTS

| | | | |
|---|---|---|---|
| 4,918,225 | A | 4/1990 | Rittner et al. |
| 5,310,477 | A | 5/1994 | Lomas |
| 6,103,948 | A | 8/2000 | Ginosar et al. |
| 6,855,856 | B2 | 2/2005 | Van Broekhoven et al. |
| 6,884,339 | B2 | 4/2005 | Benazzi et al. |
| 7,550,405 | B2 | 6/2009 | Shan et al. |
| 7,592,282 | B2 | 9/2009 | Ginosar et al. |

(Continued)

FOREIGN PATENT DOCUMENTS

| | | | |
|---|---|---|---|
| JP | 6001531 | B2 | 10/2015 |
| JP | 6042328 | B2 | 12/2016 |

(Continued)

OTHER PUBLICATIONS

International Search Report and Written Opinion in corresponding PCT Application No. PCT/US2021/062424; dated Mar. 1, 2022.

(Continued)

*Primary Examiner* — Brian A McCaig
(74) *Attorney, Agent, or Firm* — Leason Ellis LLP

(57) ABSTRACT

The present disclosure relates to a process for the hydrodealkylation of aromatic rich hydrocarbon streams to produce benzene, toluene and mixed xylenes (BTX), with high selectivity towards high value xylenes. The process uses catalysts containing a framework-substituted zirconium and/or titanium and/or hafnium-modified ultra-stable Y (USY) type zeolite.

31 Claims, 1 Drawing Sheet

(56) References Cited

U.S. PATENT DOCUMENTS

| | | |
|---|---|---|
| 7,750,197 B2 | 7/2010 | Van Broekhoven et al. |
| 7,858,069 B2 | 12/2010 | Ginosar et al. |
| 8,163,969 B2 | 4/2012 | Van Broekhoven et al. |
| 8,395,006 B2 | 3/2013 | Clark et al. |
| 8,574,542 B2 | 11/2013 | Domokos et al. |
| 8,937,205 B2 | 1/2015 | Iaccino et al. |
| 9,012,696 B2 | 4/2015 | Calaresu et al. |
| 9,145,522 B2 | 9/2015 | Negiz et al. |
| 9,150,494 B2 | 10/2015 | Tonkovich et al. |
| 9,238,599 B2 | 1/2016 | Winsett |
| 9,376,325 B2 | 6/2016 | Domokos et al. |
| 10,071,939 B2 | 9/2018 | Abudawoud |
| 10,173,950 B2 | 1/2019 | Abudawoud et al. |
| 10,427,143 B2 | 1/2019 | Domokos et al. |
| 10,293,332 B2 | 5/2019 | Koseoglu et al. |
| 2002/0016258 A1 | 2/2002 | Wu et al. |
| 2003/0168379 A1 | 9/2003 | Degnan et al. |
| 2004/0162454 A1 | 8/2004 | Gao et al. |
| 2006/0020154 A1 | 1/2006 | Lo |
| 2010/0305373 A1 | 12/2010 | Tojero et al. |
| 2011/0219671 A1 | 9/2011 | Hanks et al. |
| 2013/0175202 A1 | 7/2013 | Koseoglu et al. |
| 2014/0190868 A1 | 7/2014 | Koseoglu et al. |
| 2014/0262956 A1 | 9/2014 | Duma et al. |
| 2019/0022630 A1 | 1/2019 | Koseoglu |
| 2019/0194095 A1 | 6/2019 | Xu et al. |
| 2019/0224653 A1 | 7/2019 | Koseoglu |

FOREIGN PATENT DOCUMENTS

| | | |
|---|---|---|
| WO | 2005071045 A1 | 8/2005 |
| WO | 2017112558 A1 | 6/2017 |
| WO | 2019147345 A1 | 8/2019 |

OTHER PUBLICATIONS

Wang Yandan et al; Influence of Zirconium Modified USY on Coupled Hydrogenation and Ring Opening of Tetralin Over NiW/ USY + A1203; Catalisis Letters, J.C. Baltzer, New York, vol. 147, No. 7, May 13, 2017, pp. 1704-1713.

International Search Report and Written Opinion in corresponding PCT Application No. PCT/US2021/012268; dated Apr. 8, 2021.

International Search Report and Written Opinion in corresponding PCT Application No. PCT/US2021/064836; dated Mar. 19, 2021.

Juarez R et al: Transition metal containing zeolites and mesoporous MCM-4! as heterogeneous catalysts for the N-alkylation of 2,4-diaminotoluene with dimethylcarbonate; Catalysis Communications, Elsevier, Amsterdam, NL, vol. 10, No. 5, Jan. 25, 2009; pp. 472-476.

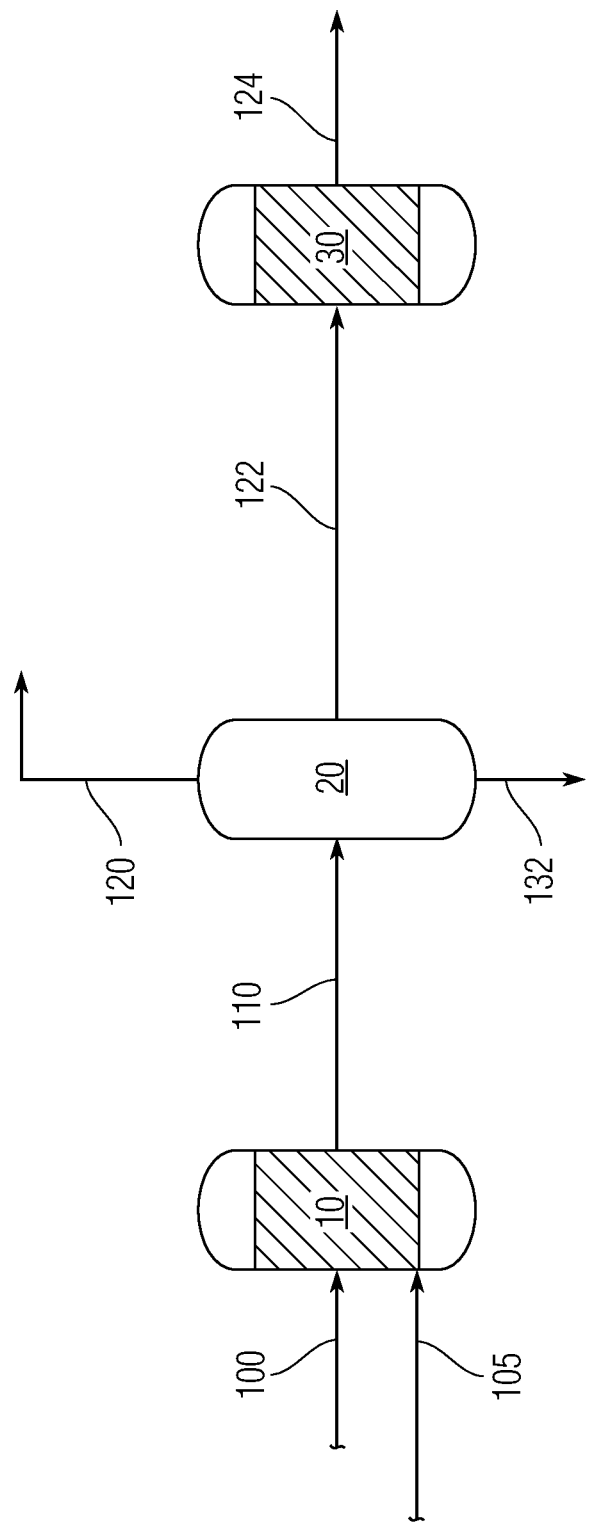

MODIFIED ULTRA-STABLE Y (USY) ZEOLITE CATALYST FOR DEALKYLATION OF AROMATICS

FIELD OF THE INVENTION

The present disclosure relates to a process for the hydrodealkylation of aromatic rich hydrocarbon streams to produce benzene, toluene and mixed xylenes (BTX), with high selectivity towards high value xylenes. The process uses catalysts containing a framework-substituted zirconium and/or titanium and/or hafnium-modified ultra-stable Y (USY) type zeolite.

BACKGROUND OF THE INVENTION

Catalytic reforming is a widely used process for refining hydrocarbon mixtures, resulting in reformate, an aromatic-rich gasoline blending fraction useful for aromatics production. The reformate from a catalytic reforming unit is sent to an aromatic complex in order to recover high value products, e.g., xylenes and benzene, and to convert lower value products, e.g., toluene, into higher value products. For example, toluene is typically recovered as a separate fraction and undergoes disproportionation to produce benzene and xylenes or is hydrodealkylated to produce benzene.

The aromatic complex produces a reject stream or bottoms that is very heavy (boiling in the range 100-450° C.), containing C9+ alkylated aromatics with alkyl groups containing 3 or more carbon number. The heavy bottoms fraction is not suitable as a gasoline blending component since it deteriorates the gasoline quality and in the long run negatively impacts engine performance. Moreover, blending is becoming more difficult due to more stringent regulations on the aromatics content in gasoline.

Para-xylene is experiencing a market grown rate of demand Consequently, the conversion of heavy aromatics to p-xylene provides a valuable product stream. It is therefore desirable to utilize the heavy reformate fraction to obtain BTX rich in xylenes via dealkylation of alkylated aromatics.

SUMMARY

Disclosed are methods and systems for hydrodealkylation of heavy, aromatic-rich reformates using a catalyst containing post-modified, framework substituted ultra-stable Y (USY) zeolite.

The present disclosure relates to a system for hydrodealkylating the bottoms stream from an aromatic recovery complex to produce benzene, toluene and xylenes (BTX), with selectivity towards high value xylenes. The process utilizes a catalyst containing post-modified, framework substituted ultra-stable Y (USY) zeolite in which titanium (Ti) and/or, zirconium (Zr) and/or hafnium (Hf) are inserted into the zeolite catalyst after dealumination. The use of modified USY zeolite catalysts according to the present disclosure results in a higher ratio of xylene to toluene and benzene compared to known processes. Thus, the process of the present disclosure provides a technical advantage in that it preferentially forms high value xylenes and reduces formation of lower value benzene and toluene.

Thus, in some embodiments, the present disclosure provides a process for hydrodealkylating a hydrocarbon feed comprising aromatic hydrocarbons with nine or more carbon atoms (C9+ aromatics), by reacting the hydrocarbon feed with a hydrogen feed in the presence of a dealkylation catalyst, wherein the dealkylation catalyst is framework-substituted ultra-stable Y (USY)-type zeolite.

In other embodiments, the present disclosure provides a process for producing mixed xylenes from a hydrocarbon feed comprising aromatic hydrocarbons with C9+ aromatics, by reacting the hydrocarbon feed with a hydrogen feed in the presence of a dealkylation catalyst which hydrodealkylates aromatic compounds in the hydrocarbon feed; wherein the dealkylation catalyst is framework-substituted ultra-stable Y (USY)-type zeolite.

In some embodiments, the framework-substituted USY zeolite is one in which a portion of aluminum atoms constituting a zeolite framework thereof is substituted with zirconium atoms and/or titanium and/or hafnium atoms. In other embodiments, the framework-substituted USY zeolite may be carried on a support which contains an inorganic oxide, e.g., alumina, silica-alumina and the like, as described herein.

Preferably, the hydrocarbon feed comprises an aromatic rich heavy reformate feed (e.g., a bottoms stream) comprising an aromatic rich hydrocarbon oil having a boiling point range of about 50° C. to about 500° C.

The process of the invention results in formation a BTX fraction with strong selectivity towards xylenes. In some embodiments, the ratio of mixed xylenes to benzene and toluene is at least about 2 to 1, preferably at least about 3 to 1. In other embodiments, the ratio of benzene to toluene to xylene is about 1:4-10:15-25.

Further embodiments and the full scope of applicability of the present disclosure will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

A more complete understanding of the invention and its many features and advantages will be attained by reference to the following detailed description and the accompanying drawing. It is important to note that the drawing illustrates only one embodiment of the present disclosure and therefore should not be considered to limit its scope.

FIG. 1 provides a diagram of an embodiment of the process.

DETAILED DESCRIPTION OF CERTAIN EMBODIMENTS

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

Described herein is a process and system for the production of mixed xylenes by hydrodealkylating a heavy hydrocarbon feed containing C9+ aromatic compounds (e.g., a heavy bottoms reformate feed). A heavy bottoms reformate feed and a hydrogen feed (e.g., hydrogen gas) are introduced to a dealkylation reactor containing a dealkylation catalyst. The dealkylation catalyst is a catalyst containing a framework-substituted ultra-stable Y (USY)-type zeolite in which a portion of aluminum atoms constituting a zeolite framework thereof is substituted with zirconium atoms and/or titanium and/or hafnium atoms. The dealkylation effluent from the dealkylation reactor may optionally be introduced to a splitter unit to separate the components of the dealkylation effluent.

Advantageously, the use of a catalyst containing a framework-substituted ultra-stable Y (USY)-type zeolite increases the overall production of xylenes as compared to other catalysts. Thus, the process results in dealkylation of C9+ aromatics to result in benzene, toluene and mixed xylene (BTX) with a preference towards high value xylenes.

Definitions

As used throughout, a reference to "C" and a number refers to the number of carbon atoms in a hydrocarbon. For example, C6 refers to a hydrocarbon with 6 carbon atoms, and C7 refers to a hydrocarbon with seven carbon atoms, and the like.

As used throughout, "C8 aromatics" refers to aromatic hydrocarbons with eight carbon atoms. Examples of C8 aromatic hydrocarbons include mixed xylenes and ethyl benzene. As used throughout, "mixed xylenes" refers to one or more of para-xylene (p-xylene), meta-xylene (m-xylene), and ortho-xylene (o-xylene).

As used throughout, "C9 aromatics" refers to aromatic hydrocarbons with nine carbon atoms. Examples of C9 aromatic hydrocarbons include methylethylbenzene, trimethylbenzene, and propylbenzene.

As used throughout, "C10+ aromatics" refers to aromatic hydrocarbons with ten carbon atoms and aromatics with more than ten carbon atoms, such as an aromatic hydrocarbon with eleven carbon atoms. C10+ aromatics can include double ring aromatic compounds. Examples of double ring aromatic compounds of C10+ aromatics include naphthalene, methylnaphthalene, naphthalene derivatives, and combinations of the same. Examples of methylnaphthalene include 1-methylnaphthalene, 2-methylnaphthalene, and combinations of the same.

As used throughout, "C9+ aromatics" refers to the group of C9 aromatics and C10+ aromatics.

As used herein, the term "BTX" means a composition comprising benzene (C6), toluene (C7) and mixed xylenes (C8). The term "xylenes" as denoted herein means any one of ortho xylene (o-xylene), meta-xylene (m-xylene), para-xylene (p-xylene) or any combination thereof. As used throughout, "mixed xylenes" refers to any one or more of o-xylene, m-xylene and p-xylene.

As used throughout, "dealkylation reaction" refers to a reaction that results in the removal of one or more alkyl groups from one or more of the reactants.

As used throughout, "light hydrocarbons" refers to one or more of alkanes, including methane, ethane, propane, butanes, pentanes, alkenes, and trace amounts of naphthenes, such as cyclopentane, cyclohexane.

As used throughout, "light gases" refers to one or more of light hydrocarbons, hydrogen, and air.

As used throughout, "single ring aromatic compounds" refers to aromatic compounds containing at least six carbon atoms arranged in a central aromatic ring and includes rings with hydrogen and hydrocarbons as substituents.

DESCRIPTION OF EMBODIMENTS

Referring to FIG. 1, an embodiment of the process for producing mixed xylenes in provided. Heavy reformate feed 100 is introduced to dealkylation reactor 10 along with hydrogen feed 105. Heavy reformate feed 100 can include toluene, mixed xylenes, C9 aromatics, and C10+ aromatics as described below.

Hydrogen feed 105 can be any stream containing hydrogen gas. Hydrogen feed 105 can be a stream of pure hydrogen from a fresh hydrogen source. In at least one embodiment, hydrogen feed 105 can be from a hydrogen source in a refinery and can contain light hydrocarbons.

Dealkylation reactor 10 can be any type of reactor capable of containing and supporting a dealkylation reaction. Dealkylation reactor 10 can be a fixed bed reactor or a fluidized bed reactor. The dealkylation temperature in dealkylation reactor 10 can be between 400 degrees Celsius (° C.) and 500° C. The dealkylation pressure in dealkylation reactor 10 can be between 20 bar (2,000 kilopascal (kPa)) and 50 bar (5,000 kPa). The liquid hourly space velocity (LHSV) can be between about 0.5 per hour ($hr^{-1}$) and about 5 $hr^{-1}$. The hydrogen to hydrocarbon ratio can be about 100 to about 500 SLt/Lt.

Dealkylation reactor 10 includes dealkylation catalyst containing a framework-substituted USY zeolite is one in which a portion of aluminum atoms constituting a zeolite framework thereof is substituted with zirconium atoms and/or titanium atoms and/or hafnium atoms, as further described below. The dealkylation catalyst can be selected to selectively convert one or more of the C9+ aromatics in dealkylation reactions. Dealkylation reactions can convert C9+ aromatics to toluene, benzene, mixed xylenes, and light gases. Reactions in dealkylation reactor 10 can remove methyl, ethyl, propyl, butyl and pentyl groups, and their isomers, attached to C9+ aromatics.

In at least one embodiment, a dealkylation catalyst can be selected to convert more than 97.5 wt % of the methylethylbenzene to toluene. In at least one embodiment, the overall conversion of C9+ aromatics can be greater than 98 wt % due to conversion of C9 aromatics and the removal of methyl, ethyl, propyl, butyl and pentyl groups attached to C10+ aromatics.

The dealkylation reaction produces a dealkylation effluent 110 which can contain mixed xylenes, toluene, benzene, light gases, and C9+ aromatics. Dealkylation effluent is then optionally introduced to splitter unit 20 which operates to separate and recover different fractions. Splitter unit 20 can be any type of separation unit capable of separating a stream into its component parts. In at least one embodiment, splitter unit 20 can be one splitter column designed to separate the feed stream into multiple split streams. In at least one embodiment, splitter unit 20 can be multiple splitter columns in series designed to separate one component from the feed stream. In at least one embodiment, splitter unit 20 can be one or more distillation units. In at least one embodiment, splitter unit 20 comprises a distillation column operating at a pressure of between 4 bar gauge (barg) and 6 barg and a temperature between 20° C. and 100° C. to separate light gases from the first column feed to produce light gas stream 120 and a liquid reaction effluent 122 comprising C6+ hydrocarbons.

In at least one embodiment, splitter unit 20 separates the components to produce light gas stream 120, and a liquid reaction effluent 122 containing BTX (C6-8 aromatic hydrocarbons) and C9+ aromatics stream. In at least one embodiment, effluent 122 can be introduced to an aromatic recovery complex (ARC) 30 wherein such effluent is further processed in order to recover BTX stream 124.

It can be understood by one of skill in the art that splitter unit 20 can be designed to operate at a temperature and pressure to produce the desired streams. In at least one embodiment, where splitter unit 20 is one distillation column, the distillation column can include multiple sections in one vessel, where each section has the operating conditions corresponding to each of the separate columns described in this paragraph.

It is apparent to a person of skill in the art that the apparatus for the hydrodealkylation process in the present disclosure is not particularly limited to the aforementioned embodiments, and that any other apparatus may be used, as long as the foregoing reactions are carried out. Various types of apparatuses may be used. In accordance with some embodiments, the process of the present disclosure may be conducted on ebullated-bed or slurry-bed or moving-bed reactors or CSTR or batch type reactors, and the like.

Hydrocarbon Feed

The hydrocarbon feed 100 used in the process of the present disclosure may be any hydrocarbon feed that is rich in aromatic hydrocarbons. In a preferred embodiment, the hydrocarbon feed is a heavy reformate feed produced from aromatic recovery processes (also designed herein "aromatics bottoms fraction"). The heavy reformate feed is preferably enriched in aromatic hydrocarbons and can include toluene, mixed xylenes, C9 aromatics, and C10+ aromatics.

In at least one embodiment, heavy reformate feed 100 can contain between 0 wt % and 10 wt % C6 aromatics (benzene). In at least one embodiment, heavy reformate feed 100 can contain between 0 wt % and 10 wt % C7 aromatics (toluene). In at least one embodiment, heavy reformate feed 100 can contain between 0 wt % and 10 wt % mixed xylenes. In at least one embodiment, heavy reformate feed 100 can contain between 0 wt % and 10 wt % C6-C8 aromatics. In at least one embodiment, heavy reformate feed 100 can contain between 0 wt % and 10 wt % mixed xylenes and between 60 wt % and 100 wt % C9+ aromatics. In at least one embodiment, heavy reformate feed 100 can contain between 0 wt % and 40 wt % C6-C8 aromatics and between 60 wt % and 100 wt % C9+ aromatics. In at least one embodiment, heavy reformate feed 100 can contain between 0 wt % and 10 wt % mixed xylenes, between 0 wt % and 10 wt % toluene, and between 80 wt % and 100 wt % C9+ aromatics. In at least one embodiment, heavy reformate feed 100 contains between 60 wt % and 100 wt % C9+ aromatics. In at least one embodiment, heavy reformate feed 100 contains between 60 wt % and 100 wt % C10+ aromatics. In at least one embodiment, heavy reformate feed 100 contains between 90 wt % and 100 wt % C10+ aromatics. In at least one embodiment, heavy reformate feed 100 contains between 60 wt % and 100 wt % C11+ aromatics. In at least one embodiment, heavy reformate feed 100 contains between 90 wt % and 100 wt % C11+ aromatics.

In at least one embodiment, heavy reformate feed 100 can include trace amounts of C8+ naphthenes and C10+ naphthylenes, including the alkyl derivatives of the same. In further embodiments, heavy reformate feed includes trace amounts of non-aromatic hydrocarbons. In at least one embodiment, heavy reformate feed 100 contains between 0 wt % and 1 wt % C4-C12 n-paraffins. In at least one embodiment, heavy reformate feed 100 contains between 0 wt % and 1 wt % C4-C12 i-paraffins. In at least one embodiment, heavy reformate feed 100 contains between 0 wt % and 1 wt % C8+ naphthenes and C10+ naphthylenes.

In some embodiments, the heavy reformate feed comprises an aromatic rich hydrocarbon oil having a boiling point range of about 50° C. to about 500° C. In other embodiments, the hydrocarbon feed comprises an aromatic rich hydrocarbon oil having a boiling point range of about 100° C. to about 500° C. In other embodiments, the heavy reformate feed comprises an aromatic rich hydrocarbon oil having a boiling point range of about 150° C. to about 500° C. In other embodiments, the heavy reformate feed comprises an aromatic rich hydrocarbon oil having a boiling point range of about 150° C. to about 400° C.

Reformate feeds usually contain very low amount of sulfur, as they are typically subjected to desulfurization prior to reforming such that the resulting gasoline product contains an acceptable level of sulfur for compliance with current sulfur specification. In some embodiments, the dealkylated hydrocarbon product preferably contains less than about 500 ppm sulfur, preferably less than about 10 ppm, most preferably less than about 0.5 ppm. In other embodiments, the dealkylated hydrocarbon product containing less than about 100 ppm nitrogen, preferably less than about 10 ppm, most preferably less than about 0.5 ppm.

Dealkylated Product

As a result of the dealkylation reaction, the amount of alkylated aromatics is reduced relative to the amount of alkylated aromatics in the initial feed. According to at least one embodiment, the hydrocarbon feed is dealkylated at least about 50%. According to at least one embodiment, the hydrocarbon feed is dealkylated at least about 60%. According to at least one embodiment, the hydrocarbon feed is dealkylated at least about 70%.

Advantageously, the process of the present disclosure produces a dealkylated product comprising benzene, toluene, mixed xylenes (BTX), C9 aromatics and C10+ aromatics. Optionally, the dealkylated product contains trace amounts of C8+ naphthenes, C10+ naphthylenes, C4-C12 n-paraffins and/or C4-C12 i-paraffins.

Advantageously, the process of the present disclosure is characterized by production of a BTX fraction with strong selectivity towards xylene relative to benzene and toluene. Thus, in at least one embodiment, the process produces a higher amount of mixed xylenes compared with benzene and toluene. In at least one embodiment, the ratio of mixed xylenes to benzene and toluene is at least about 2 to 1. In at least one embodiment, the ratio of mixed xylenes to benzene and toluene is preferably at least about 3 to 1.

In other embodiments, the ratio of benzene to toluene to xylene is about 1:4-10: 15-25 (expressed as benzene:toluene:xylene, and normalized to benzene). In other embodiments, the ratio of benzene to toluene to xylene is about 1:4-7:18-25.

Catalyst with Framework Substituted Ultra Stable Y (USY) Zeolite

Dealkylation reactor 10 can include a dealkylation catalyst. Advantageously, the dealkylation catalyst contains a framework substituted zeolite in which a part of aluminum atoms constituting a zeolite framework is substituted with zirconium atoms and/or titanium atoms and/or hafnium atoms.

In some embodiments, the catalyst with the framework-substituted zeolite catalyst used in the process of the present disclosure is an ultra-stable Y-type zeolite in which silicon atoms and aluminum atoms form a zeolite framework and in which a part of the aluminum atoms is substituted with zirconium atoms and/or titanium atoms and/or hafnium atoms. For example, the framework-substituted zeolite in the catalyst in which a part of aluminum atoms forming a zeolite framework is substituted only with zirconium atoms is referred to as a "zirconium-substituted zeolite" or "Zr-USY"; the framework-substituted zeolite in the catalyst in which a part of aluminum atoms forming a zeolite framework of the framework-substituted zeolite is substituted only with titanium atoms is referred to as a "titanium-substituted zeolite" or "Ti-USY"; the framework-substituted zeolite in the catalyst in which a part of aluminum atoms forming a zeolite framework is substituted only with zirconium atoms and titanium atoms is referred to as a "zirconium.titanium-substituted zeolite" or "Zr—Ti-USY"); and the framework-substituted zeolite in the catalyst in which a part of aluminum atoms forming a zeolite framework is with zirconium atoms, titanium and hafnium atoms is referred to as "zirconium.titanium.hafnium substituted zeolite" or "Zr.Ti.Hf-USY".

Zirconium atoms and/or titanium and/or hafnium atoms which are substituted for the aluminum atoms forming a framework of the ultra-stable Y-type zeolite serve as constituents of the framework of the ultra-stable Y-type zeolite. Substitution can be verified by, e.g., ultraviolet, visible, and near-infrared spectrophotometry (UV-Vis-NIR), Fourier transform infrared spectroscopy (FT-IR.

In some embodiments, in addition to the substituted atoms, the zirconium atoms and/or titanium and/or hafnium atoms may further be attached (carried) to the outside of, or combined with the framework of the USY-type catalyst, as described in U.S. Pat. No. 10,293,332, which is hereby incorporated by reference in its entirety as if fully set forth herein.

In some embodiment, the framework-substituted zeolite of the catalyst contains about 0.1% to about 5%, preferably about 0.2% to about 4%, more preferably about 0.3% to about 3% zirconium atoms and/or titanium and/or hafnium atoms by mass in terms of oxide (i.e., "$ZrO_2$", "$TiO_2$" and "$HfO_2$") based on the framework-substituted zeolite. As contemplated herein, a content range (based on oxides) of zirconium atoms and/or titanium and/or hafnium atoms includes all of the contents of zirconium atoms and/or titanium and/or hafnium atoms substituted for aluminum atoms forming a zeolite framework and zirconium atoms and/or titanium and/or hafnium atoms which are not substituted for the above aluminum atoms.

It is appreciated by a person of skill in the art, that when the framework-substituted zeolite in the catalyst contains the zirconium atoms and the titanium atoms and/or the hafnium atoms described above, a mass ratio (in terms of oxides) of the zirconium atoms to the titanium atoms and/or the hafnium atoms is not specifically be restricted, and any ratio of zirconium or titanium or hafnium that is effective to carry out the process of the present invention may be used.

The zirconium atom and/or titanium and/or hafnium atom content of the framework-substituted zeolite in the catalyst can be measured with, for example, an X-ray fluorescence analyzer, a high frequency plasma emission spectrometer, an atomic absorption spectrometer or the like.

In some embodiments, particles of the zirconium and/or titanium and/or hafnium-modified USY catalyst have a diameter of 50 nm or less.

Method for Producing the Framework-Substituted Zeolite

The framework-substituted zeolite in the catalyst in the present invention can be produced in accordance with the methods described by U.S. Pat. No. 10,293,332. For example, the framework-substituted zeolite in the catalyst may be produced by firing a USY-type zeolite at 500° C. to 700° C., the USY-type zeolite having a crystal lattice constant of 2.430 to 2.450 nm, a specific surface area of 600 to 900 m²/g, and a molar ratio of $SiO_2$ to $Al_2O_3$ of 20 to 100, forming a suspension containing the fired USY-type zeolite, the suspension having a liquid/solid mass ratio of 5 to 15, adding an inorganic acid or an organic acid so that a pH of the above suspension is 1.0 to 2.0, subsequently adding a solution containing a zirconium compound and/or a hafnium compound and mixing them and neutralizing the solution with, for example, an aqueous ammonia in such a manner that the mixed solution has a pH of about 7.

Ultra-stable Y-type zeolite is used as one of the raw materials for preparing the framework-substituted zeolite in the catalyst. Ultra-stable Y-type zeolite means zeolite having a crystal lattice constant (UD) falling in a range of 2.430 nm or more and 2.450 nm or less, a specific surface area of 600 to 900 m²/g and a molar ratio (silica-alumina ratio) falling in a range of 20 to 100 in terms of $SiO_2$ to $Al_2O_3$. The ultra-stable Y-type zeolite may be prepared by any method known in the art.

In the method for producing the framework-substituted ultra-stable Y-type zeolite, extraskeletal aluminum (aluminum atoms which do not form the zeolite framework) may be removed from the ultra-stable Y-type zeolite raw material in order to obtain the ultra-stable Y-type zeolite. Extraskeletal aluminum can be removed by, for example, a method of dispersing the ultra-stable Y-type zeolite in warm water of 40 to 95° C. to prepare a suspension, adding sulfuric acid to the above suspension and stirring it for 10 minutes to 3 hours while maintaining the temperature at 40 to 95° C. to thereby dissolve the extraskeletal aluminum. After dissolving the extraskeletal aluminum, the suspension is filtrated, and a residue on the filter is washed with purified water of 40 to 95° C. and dried at 100 to 180° C. for 3 to 30 hours, whereby an ultra-stable Y-type zeolite from which the extraskeletal aluminum is removed can be obtained.

Furthermore, in the method for producing the framework-substituted ultra-stable Y-type zeolite, the ultra-stable Y-type zeolite raw material may be calcined at 500° C. to 700° C., preferably 550° C. to 650° C. The calcining time shall not specifically be restricted as long as the targeted framework-substituted zeolite is obtained, and it is calcined in a range of, for example, 30 minutes to 10 hours. In respect to a calcining atmosphere of the ultra-stable Y-type zeolite, it is carried out preferably in the air. The calcined ultra-stable Y-type zeolite is suspended in water having a temperature of about 20° C. to about 30° C. to form a suspension. With respect to the concentration of the suspension of the ultra-stable Y-type zeolite, the liquid/solid mass ratio is preferably in the range of 5 to 15, and more preferably, a mass ratio of 8 to 12 is recommended.

Next, an inorganic acid or an organic acid is added thereto so that a pH of the suspension described above is controlled to 1.0 to 2.0, and subsequently a solution containing a zirconium compound and/or a hafnium compound is added and mixed. Then, the mixed solution is neutralized (pH 7.0 to 7.5) and dried desirably at 80 to 180° C., whereby the framework-substituted zeolite described above can be obtained.

Sulfuric acid, nitric acid, hydrochloric acid and the like can be given as the above inorganic acid used, and among them, sulfuric acid, hydrochloric acid and the like are particularly preferred. Further, carboxylic acids can suitably be used as the organic acid described above. A use amount of the inorganic acid or the organic acid shall not be restricted as long as a pH of the suspension can be controlled to a range of 1.0 to 2.0, and it is, for example, a 0.5- to 4.0-fold molar amount and preferably 0.7- to 3.5-fold molar amount based on an amount of $Al_2O_3$ in the ultra-stable Y-type zeolite, but it shall not be restricted to the above range.

Examples of the zirconium compound described above include zirconium sulfate, zirconium nitrate, zirconium chloride and the like. Among these compounds, zirconium sulfate, zirconium nitrate, and the like are particularly preferred. The amount of the zirconium compound added is preferably about 0.1% to about 5% by mass and more preferably about 0.2% to about 4% by mass on a zirconium oxide basis with respect to the ultra-stable Y-type zeolite described above. Usually, an aqueous solution of a zirconium compound prepared by dissolving the zirconium compound in water is suitably used as the zirconium compound.

Examples of the hafnium compound described above include hafnium chloride, hafnium nitrate, hafnium fluoride, hafnium bromide, hafnium oxalate and the like. Among these compounds, hafnium chloride, hafnium nitrate, and the like are particularly preferred. The amount of the hafnium compound added is preferably about 0.1% to about 5% by mass and more preferably about 0.2% to about 4% by mass on a hafnium oxide basis with respect to the ultra-stable Y-type zeolite. Usually, an aqueous solution of a hafnium compound prepared by dissolving the hafnium compound in water is suitably used as the hafnium compound.

In some embodiments, a titanium compound may be added to the mixed solution described above. Examples of the titanium compound include titanium sulfate, titanium acetate, titanium chloride, titanium nitrate, and titanium lactate. Among these compounds, titanium sulfate, titanium acetate, and the like are particularly preferred. The amount of the titanium compound added is preferably about 0.1% to about 5% by mass and more preferably about 0.2% to about 4% by mass on an oxide basis with respect to the ultra-stable Y-type zeolite. Usually, an aqueous solution of a titanium compound prepared by dissolving the titanium compound in water is suitably used as the titanium compound.

A pH of the above suspension has to be controlled in advance to 1.0 to 2.0 for the purpose of preventing precipitation from being generated in mixing an aqueous solution of the zirconium compound, the hafnium compound or the titanium compound with a suspension of the ultra-stable Y-type zeolite described above.

In the case of mixing an aqueous solution of the zirconium compound, the hafnium compound or the titanium compound with a suspension of the ultra-stable Y-type zeolite, preferably, the above aqueous solution is gradually added to the suspension. After finishing addition of the aqueous solution described above to the suspension, the solution is preferably mixed by stirring at, for example, room temperature (about 25° C. to about 35° C.) for 3 to 5 hours. Further, after finishing the mixing described above, the mixed solution described above is neutralized by adding an alkali such as aqueous ammonia and the like so that a pH thereof is controlled to 7.0 to 7.5, whereby the framework-substituted zeolite in the catalyst can be obtained.

It is apparent to a person of skill in the art, that when only the zirconium compound (or an aqueous solution thereof) is used as the compound (or an aqueous solution thereof) added to the suspension described above, the framework-substituted zeolite in the catalyst (Zr-USY) in which zirconium atoms is substituted for a part of aluminum atoms forming the framework of the ultra-stable Y-type zeolite is formed; when only the hafnium compound (or an aqueous solution thereof) is used, the framework-substituted zeolite in the catalyst (Hf-USY) in which hafnium atoms is substituted for a part of aluminum atoms forming the framework of the ultra-stable Y-type zeolite is formed; when only the titanium compound (or an aqueous solution thereof) is used, the framework-substituted zeolite in the catalyst (Ti-USY) in which titanium atoms is substituted for a part of aluminum atoms forming the framework of the ultra-stable Y-type zeolite is formed; when the zirconium compound and the titanium compound (or aqueous solutions thereof) are used, the framework-substituted zeolite in the catalyst (Zr.Ti-USY) in which zirconium atoms and titanium atoms are substituted for a part of aluminum atoms forming the framework of the ultra-stable Y-type zeolite is formed; when the zirconium compound and the hafnium compound (or aqueous solutions thereof) are used, the framework-substituted zeolite in the catalyst (Zr.Hf-USY) in which zirconium atoms and hafnium atoms are substituted for a part of aluminum atoms forming the framework of the ultra-stable Y-type zeolite is formed; and when the zirconium compound, the titanium compound and the hafnium compound (or aqueous solutions thereof) are used, the framework-substituted zeolite in the catalyst (Zr.Ti Hf-USY) in which zirconium atoms, titanium atoms and hafnium atoms are substituted for a part of aluminum atoms forming the framework of the ultra-stable Y-type zeolite is formed.

The resulting framework-substituted zeolite in the catalyst is preferably filtered, if desired, washed with water, and dried at about 80° C. to about 180° C.

The framework-substituted USY zeolite may be carried on a support which contains an inorganic oxide excluding the above framework-substituted zeolite in the catalyst in addition to the framework-substituted zeolite in the catalyst described above. The inorganic oxide typically contains a substance serving as a granulating agent or a binder. Usually, a known substance that is contained in a support including the ultra-stable Y-type zeolite and that is used as a granulating agent or the like can be used. Examples of inorganic oxides include, but are not limited to alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In the present disclosure, in particular, an inorganic oxide mainly composed of alumina, silica-alumina is preferred.

The content of the framework-substituted zeolite in the catalyst and the inorganic oxide content of the support can be appropriately determined according to the object. The support includes a framework-substituted zeolite in the catalyst of about 2% to about 80% by mass, preferably about 10% to about 80% by mass, and more preferably about 20% to about 70% by mass, and an inorganic oxide content of about 98% to about 20% by mass, preferably about 90% to about 20% by mass and more preferably about 80% to about 30% by mass.

Metal Component:

The catalyst used in the process of the present disclosure may further include active metal components selected from the group consisting of IUPAC Group 6 to 11 metals of the Periodic Table. Examples of active metals include iron, cobalt, nickel, rhodium, palladium, silver, iridium, platinum or gold in group 8 of the long periodic table and/or metal components chromium, molybdenum or tungsten in group 6. Preferred examples of the metal component include combinations of molybdenum or tungsten in group 6 and cobalt or nickel in group 8; and metal components of the platinum group (platinum, rhodium, palladium and the like).

When present, the metal component may be contained in the catalyst in an amount of about 0.0001 to about 40% by mass in terms of oxide. In the case of molybdenum, tungsten, cobalt or nickel, an amount thereof is particularly preferably about 3 to about 30% by mass in terms of oxide based on a mass of the catalyst. In the case of the platinum group (platinum, rhodium, palladium and the like), when present, an amount thereof is particularly preferably about 0.01 to about 2% by mass in terms of metal.

EXAMPLES

The following examples are provided to better illustrate embodiments of the present disclosure. However, it is to be understood that these examples are merely illustrative in nature, and that the process embodiments of the present disclosure are not necessarily limited thereto.

Example 1

Example 1 provides an analysis of a dealkylation reactor 10 with reference to FIG. 1. Heavy reformate feed 100 has the composition of Table 1. The feedstock composition and properties are summarized in Table 1. Detail composition obtained from PIONA analysis is shown in Table 2.

TABLE 1

| Feedstock properties. | | |
|---|---|---|
| Property (unit) | Unit | Value |
| Density @ 15° C. | Kg/L | 0.84 |
| Carbon | W % | 89.85 |
| Hydrogen | W % | 10.15 |
| Sulfur | W % | 1.42 |
| Nitrogen | ppmw | 73 |
| Distillation (D2887) | | |
| IBP | ° C. | 91 |
| 10 W % | ° C. | 187 |
| 30 W % | ° C. | 253 |
| 50 W % | ° C. | 293 |
| 70 W % | ° C. | 331 |
| 90 W % | ° C. | 381 |
| FBP | ° C. | 441 |

TABLE 2

| Feedstock compound type composition (W %) | | | | | | | | | | |
|---|---|---|---|---|---|---|---|---|---|---|
| | Carbon Number | | | | | | | | | |
| | 4 | 5 | 6 | 7 | 8 | 9 | 10 | 11 | 12+ | Total |
| n-Paraffins | 0.00 | 0.00 | 0.00 | 0.00 | 0.00 | 0.00 | 0.00 | 0.00 | 0.00 | 0.00 |
| i-Paraffins | 0.00 | 0.00 | 0.00 | 0.00 | 0.00 | 0.00 | 0.03 | 0.04 | 0.30 | 0.37 |
| Naphtenes | 0.00 | 0.00 | 0.00 | 0.00 | 0.00 | 0.00 | 0.00 | 0.00 | 0.07 | 0.07 |
| Aromatics | 0.00 | 0.00 | 0.00 | 0.06 | 1.04 | 84.20 | 11.08 | 3.18 | 0.00 | 99.56 |
| Total | 0.00 | 0.00 | 0.00 | 0.06 | 1.04 | 84.20 | 11.11 | 3.22 | 0.37 | 100.00 |

The pilot plant test conditions are summarized in Table 3.

TABLE 3

| Operating Conditions | | |
|---|---|---|
| Variable | Unit | Value |
| Catalyst | | Ni—Mo/Ti—Zr—modified USY Zeolite |
| Temperature | ° C. | 400, 425 |
| LHSV | h$^{-1}$ | 1.0 |
| H2/Oil Ratio | SLt/L | 200, 400 t |
| Hydrogen Partial Pressure | bar | 30 s |

The catalyst was a framework-substituted ultra-stable Y (USY)-type zeolite in which a portion of aluminum atoms constituting a zeolite framework thereof is substituted with zirconium atoms and titanium atoms, which further includes Nickel (Ni) and Molybdenum (Mo) as active metals.

Results:

Aromatic dealkylation results are shown in Table 4 (reaction temperature: 400° C.) and Table 5 (reaction temperature: 425° C.):

TABLE 4 dealkylation results at 400° C.

| | Carbon Number | | | | | | | | | |
|---|---|---|---|---|---|---|---|---|---|---|
| | 4 | 5 | 6 | 7 | 8 | 9 | 10 | 11 | 12+ | Total |
| n-Paraffins | 0.00 | 0.03 | 0.02 | 0.00 | 0.00 | 0.00 | 0.00 | 0.00 | 0.00 | 0.05 |
| i-Paraffins | 0.04 | 0.13 | 0.12 | 0.04 | 0.04 | 0.06 | 0.00 | 0.00 | 0.13 | 0.56 |
| Naphtenes | 0.03 | 0.36 | 0.47 | 0.73 | 1.29 | 0.18 | 0.00 | 0.00 | 0.00 | 3.06 |
| Aromatics | 0.00 | 0.00 | 1.34 | 8.96 | 26.07 | 45.05 | 11.84 | 3.07 | 0.00 | 96.33 |
| Total | 0.07 | 0.53 | 1.95 | 9.73 | 27.4 | 45.3 | 11.84 | 3.07 | 0.13 | 100.00 |

TABLE 5 dealkylation results at 425° C.

| | Carbon Number | | | | | | | | | |
|---|---|---|---|---|---|---|---|---|---|---|
| | 4 | 5 | 6 | 7 | 8 | 9 | 10 | 11 | 12+ | Total |
| n-Paraffins | 0.00 | 0.03 | 0.01 | 0.00 | 0.00 | 0.00 | 0.00 | 0.00 | 0.00 | 0.04 |
| i-Paraffins | 0.02 | 0.06 | 0.06 | 0.02 | 0.02 | 0.04 | 0.00 | 0.00 | 0.12 | 0.34 |
| Naphtenes | 0.02 | 0.16 | 0.18 | 0.25 | 0.51 | 0.00 | 0.00 | 0.00 | 0.00 | 1.12 |
| Aromatics | 0.00 | 0.00 | 2.03 | 10.08 | 44.26 | 29.75 | 9.14 | 3.24 | 0.00 | 98.5 |
| Total | 0.04 | 0.25 | 2.29 | 10.35 | 44.79 | 29.79 | 9.14 | 3.24 | 0.13 | 100.00 |

The benzene/toluene/xylene ratio obtained according to the Experiment in Table 4 is summarized in Table 6.

TABLE 6

Dealkylation results at 400° C. (Table 4)

| | wt. % | % | Ratio (normalized to toluene) |
|---|---|---|---|
| Benzene | 1.34 | 3.7 | 1 |
| Toluene | 8.96 | 24.6 | 6.7 |
| Xylenes | 26.07 | 71.7 | 19.5 |

The benzene/toluene/xylene ratio obtained according to the Experiment in Table 5 is summarized in Table 7.

TABLE 7

Dealkylation results at 425° C.

| | wt. % | % | Ratio (normalized to toluene) |
|---|---|---|---|
| Benzene | 2.03 | 3.6 | 1 |
| Toluene | 10.08 | 17.9 | 5 |
| Xylenes | 44.26 | 78.5 | 21.8 |

Comparative Example

Table 8 provides the benzene/toluene/xylene ratio obtained according to the process of US 2019/0194095, Example 1. The process of US 2019/0194095 uses a ZSM-5 zeolite catalyst at 400° C. US 2019/0194095 is hereby expressly incorporated by reference in its entirety.

TABLE 8

US 2019/0194095 (COMPARATIVE)

| | wt. % | % | Ratio (normalized to toluene) |
|---|---|---|---|
| Benzene | 2.49 | 7.1 | 1 |
| Toluene | 16.26 | 46.1 | 6.5 |
| Xylenes | 16.49 | 46.8 | 6.6 |

As seen, the process of the present disclosure produces a product having a benzene:toluene:xylene ratio of 1.0:6.7:19.5 at 400° C. and 1.0:5.0:21.8 at 425° C., while the process of US 2019/0194095 results in a benzene:toluene:xylene ratio of 1:0:6.5:6.6 at 400° C.

Thus, according to the process of US 2019/0194095, which uses a ZSM-5 catalyst, the ratio/selectivity toward toluene and xylenes are similar. However, in the process of the present disclosure, which uses framework-substituted ultra-stable Y (USY)-type zeolite, there is a strong selectivity towards xylenes over benzene and toluene. Thus, the use of modified USY zeolite catalysts according to the present disclosure provides a technical advantage, in that it results in a higher ratio of desired, high value xylenes, as compared with toluene and benzene.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for hydrodealkylating a hydrocarbon feed to produce a dealkylated product, the process comprising the step of reacting the hydrocarbon feed with a hydrogen feed in the presence of a dealkylation catalyst, wherein the hydrocarbon feed comprises aromatic hydrocarbons with nine or more carbon atoms (C9+ aromatics; and wherein the dealkylation catalyst is a framework-substituted ultra-stable Y (USY)-type zeolite in which a portion of aluminum atoms constituting a zeolite framework thereof is substituted with zirconium atoms and/or titanium and/or hafnium atoms.

2. The process according to claim 1, further comprising the steps of:
 introducing the hydrocarbon feed and the hydrogen feed to a dealkylation reactor, wherein the dealkylation reactor comprises the dealkylation catalyst; and
 reacting the hydrocarbon feed with the hydrogen feed in the presence of the dealkylated catalyst to produce a dealkylated product.

3. The process according to claim 1, wherein the framework-substituted USY-type zeolite in the catalyst comprises zirconium atoms and titanium atoms.

4. The process according to claim 1, wherein the framework-substituted USY-type zeolite in the catalyst comprises from about 0.1 to about 5% by mass zirconium and/or titanium and/or hafnium atoms, each calculated as the oxide basis.

5. The process according to claim 1, wherein the framework-substituted USY-type zeolite in the catalyst further includes a support comprising inorganic oxides selected from the group consisting of alumina, silica-alumina and combinations thereof.

6. The process according to claim 1, wherein the framework-substituted USY-type zeolite in the catalyst further includes alumina as a binder.

7. The process according to claim 1, wherein the catalyst further includes an active metal selected from the group consisting of IUPAC Group 6 to 11 metal of the Periodic Table.

8. The process according to claim 1, wherein the dealkylated product comprises benzene, toluene, mixed xylenes (BTX), and C9+ aromatics.

9. The process according to claim 8, wherein the mixed xylenes are produced at a higher amount compared with benzene and toluene.

10. The process according to claim 9, wherein the ratio of mixed xylenes to benzene and toluene is at least 2 to 1, expressed as the ratio of mixed xylenes:benezene+toluene.

11. The process according to claim 10, wherein the ratio of mixed xylenes to benzene and toluene is at least about 3 to 1, expressed as the ratio of mixed xylenes:benzene+toluene.

12. The process according to claim 9, wherein the ratio of benzene to toluene to xylene in the dealkylated product is about 1: 4-10:15-25.

13. The process according to claim 1, wherein the hydrocarbon feed comprises an aromatic rich hydrocarbon oil having a boiling point range of about 50° C. to about 500° C.

14. The process according to claim 1, wherein the hydrocarbon feed comprises an aromatic rich heavy reformate feed.

15. The process according to claim 1, which is operated at reaction temperature range of about 400° C. to about 500° C., a pressure of about 20 to about 50 bars, a LHSV of about 0.5 to about 5 h$^{-1}$, and a hydrogen to hydrocarbon ratio of about 100 to about 500 SLt/Lt.

16. The process according to claim 15, which is operated at reaction temperature range of about 400° C. to about 425° C.

17. The process according to claim 1, wherein the hydrogen feed comprises hydrogen gas.

18. The process according to claim 1, wherein the dealkylated product contains less than about 500 ppm sulfur.

19. The process according to claim 18, wherein the dealkylated product contains less than about 10 ppm sulfur.

20. The process according to claim 19, wherein the dealkylated product contains less than about 0.5 ppm sulfur.

21. The process according to claim 1, wherein the dealkylated product contains less than about 100 ppm nitrogen.

22. The process according to claim 21, wherein the dealkylated product contains less than about 10 ppm nitrogen.

23. The process according to claim 22, wherein the dealkylated product contains less than about 0.5 ppm nitrogen.

24. The process according to claim 1, wherein the hydrocarbon feed is dealkylated at least about 50 wt %.

25. The process according to claim 24, wherein the hydrocarbon feed is dealkylated at least about 60 wt %.

26. The process according to claim 25, wherein the hydrocarbon feed is dealkylated at least about 70 wt %.

27. The process according to claim 1, further comprising the steps of introducing the dealkylated product into a splitter unit and separating the dealkylated product into a light hydrocarbon stream, and a stream comprising C6+ aromatic hydrocarbons.

28. The process according to claim 27, wherein the C6+ aromatic hydrocarbon stream comprises benzene, toluene, mixed xylene (BTX) and C9+ aromatic hydrocarbons.

29. The process according to claim 28, further comprising the step of introducing the C6+ aromatic hydrocarbon stream into an aromatic recovery complex (ARC) to recover BTX.

30. A process for producing mixed xylenes from a hydrocarbon feed, the process comprising the step of reacting the hydrocarbon feed with a hydrogen feed in the presence of a dealkylation catalyst which hydrodealkylates aromatic hydrocarbons in the hydrocarbon feed; wherein the hydrocarbon feed comprises aromatic hydrocarbons with nine or more carbon atoms (C9+ aromatics); and wherein the dealkylation catalyst is framework-substituted ultra-stable Y (USY)-type zeolite in which a portion of aluminum atoms constituting a zeolite framework thereof is substituted with zirconium atoms and/or titanium and/or hafnium atoms.

31. The process according to claim 30, wherein the hydrocarbon feed is a heavy reformate feed.

* * * * *